(12) United States Patent
Pass et al.

(10) Patent No.: US 8,569,450 B2
(45) Date of Patent: Oct. 29, 2013

(54) CD3 EPSILON IMMUNOGENS AND ANTIBODIES

(75) Inventors: Kenneth A. Pass, Glenmont, NY (US); Barbara Lindau-Shepard, Albany, NY (US); David K. Janik, Deer Park, NY (US)

(73) Assignee: Health Research Inc., Menands, NY (US)

( * ) Notice: Subject to any disclaimer, the term of this patent is extended or adjusted under 35 U.S.C. 154(b) by 299 days.

(21) Appl. No.: 13/039,722

(22) Filed: Mar. 3, 2011

(65) Prior Publication Data

US 2011/0217790 A1    Sep. 8, 2011

Related U.S. Application Data

(60) Provisional application No. 61/310,199, filed on Mar. 3, 2010, provisional application No. 61/377,833, filed on Aug. 27, 2010, provisional application No. 61/434,745, filed on Jan. 20, 2011.

(51) Int. Cl.
*A61K 38/04* (2006.01)

(52) U.S. Cl.
USPC ............................................. 530/327

(58) Field of Classification Search
None
See application file for complete search history.

(56) References Cited

U.S. PATENT DOCUMENTS

2004/0018493 A1    1/2004    Anastasio et al.

FOREIGN PATENT DOCUMENTS

WO    WO 02083921 A2 * 10/2002

OTHER PUBLICATIONS

Genevieve de Saint Basile, et al., Severe Combined Immunodeficiency Caused by Deficiency in Either the δ or the ε Subunit of CD3, Journal of Clinical Investigation (2004) vol. 114, No. 10. p. 1512-1517.

* cited by examiner

*Primary Examiner* — Zachary Skelding
(74) *Attorney, Agent, or Firm* — Vedder Price P.C.; Thomas J. Kowalski; Deborah L. Lu

(57) ABSTRACT

The present invention relates to novel CD3 epsilon peptides, antibodies against the novel CD3 epsilon peptides. The invention also relates to methods of identifying an immunodeficiency (such as severe combined immunodeficiency (SCID) or a T cell immunodeficiency) in a patient, which may involve antibodies against CD3 epsilon peptides.

2 Claims, 9 Drawing Sheets

AKAKPVTRGAGA (SEQ ID NO: 1)

LYSGLNQRRI (SEQ ID NO: 2)

FIG. 1

TREC tested specimens and controls

| Number of cells x $10^6$ | | | |
|---|---|---|---|
| CD3 | CD45 | Classification | Diagnosis |
| Low | 0.7 | Positive | ADA |
| 4.1 | 0.4 | Negative | Ctrl |
| 10.8 | High | Negative | Ctrl |
| Low | 3.3 | Positive | PNP |
| 5.5 | 3.6 | Negative | Ctrl |
| 0.4 | 6.5 | Positive | X-linked |
| Low | 3.3 | Positive | X-linked |
| Low | 2.3 | Positive | X-linked |

FIG. 3

Ranges

| CD3 | | 1 - 13 x 10⁶ cells / mL | | | | 1.5 - 9.1 x 10⁶ cells / mL | |
|---|---|---|---|---|---|---|---|
| CD45 | | 2.1 - 34 x 10⁶ cells / mL | | | | 0.5 - 9.7 x 10⁶ cells / mL | |
| Random Infants | | | | Normal birth weight infants | | Low birth weight infants | |
| Number of cells x 10⁶ | | | | Number of cells x 10⁶ | | Number of cells x 10⁶ | |
| CD3 | CD45 | CD3 | CD45 | CD3 | CD45 | CD3 | CD45 |
| 4.2 | 6.4 | 6.8 | High | 4.2 | 14.2 | 3.9 | 5.3 |
| 7 | High | 4.7 | 6.8 | 6.9 | 10.8 | 1.5 | 0.5 |
| 8.4 | High | 8.9 | High | 5.6 | 9.1 | 7.4 | ? |
| 6.5 | 8.1 | 5.2 | 4 | 8.7 | 11.4 | 4.1 | 2.6 |
| 13 | High | 9.2 | 9.7 | 7.6 | 13.4 | 6.7 | 6.6 |
| 7.3 | 7.5 | 11.5 | High | 9.9 | 12.7 | 5.8 | 7.7 |
| 1.7 | 2.1 | 7.2 | 11.2 | 6.6 | High | 9.1 | 5.6 |
| 8 | High | 6.8 | 9.9 | .7 | High | 8.7 | 9.7 |
| 9.5 | High | 6.1 | High | 4.2 | 5 | 6.9 | 6.1 |
| 7.9 | 9.6 | 8.8 | 11.4 | 7.4 | 7.8 | 5.1 | 3.9 |
| 4.3 | 6.3 | 11.2 | High | | | | |
| 4.5 | High | 7 | 8.7 | | | | |
| 4.2 | 10.7 | 7.1 | High | | | | |
| 7.4 | 6.9 | 1 | 5.8 | | | | |
| 10.1 | 10.9 | | | | | | |

FIG. 4

| Substitution | % Original 1 | Substitution | % Original 2 |
|---|---|---|---|
| AKAKPVTRGAGA | 100 | LYSGLNQRRI | 100 |
| VKAKPVTRGAGA | 105 | AYSGLNQRRI | 107 |
| AAAKPVTRGAGA | 102 | LASGLNQRRI | 104 |
| AKVKPVTRGAGA | 102 | LYAGLNQRRI | 100 |
| AKAAPVTRGAGA | 100 | LYSALNQRRI | 100 |
| AKAKAVTRGAGA | 93 | LYSGANQRRI | 101 |
| AKAKPATRGAGA | 100 | LYSGLAQRRI | 77 |
| AKAKPVARGAGA | 95 | LYSGLNARRI | 52 |
| AKAKPVTAGAGA | 61 | LYSGLNQARI | 81 |
| AKAKPVTRAAGA | 38 | LYSGLNQRAI | 22 |
| AKAKPVTRGVGA | 40 | LYSGLNQRRA | 53 |
| AKAKPVTRGAAA | 44 | | |
| AKAPVTERGAGV | 63 | | |

FIG. 5B

| Number | sex (m/f) | Diagnosis | MFI | 1 x 10^6 CD3+ cells/mL |
|---|---|---|---|---|
| 1 | M | Wiskott Aldrich Syndrome | 912 | 0.5 |
| 9 | M | Omenn Syndrome | 394 | LOW |
| 17 | M | SCID | 180 | LOW |
| 29 | M | SCID | 282 | LOW |
| 41 | F | SCID | 125 | LOW |
| 81 | F | SCID (25% maternal engraftment) | 1547 | 1.1 |
| 93 | F | SCID | 1265 | 1.0 |
| 97 | M | SCID | 990 | 0.7 |
| 101 | M | SCID | 420 | LOW |
| 113 | M | SCID | 644 | 0.3 |
| 117 | M | SCID | 289 | LOW |

FIG. 8

CD3 EPSILON IMMUNOGENS AND ANTIBODIES

INCORPORATION BY REFERENCE

This application claims priority to U.S. provisional patent application Ser. Nos. 61/310,199 filed Mar. 3, 2010, 61/377,833 filed Aug. 27, 2010 and 61/434,745 filed Jan. 20, 2011.

FEDERAL FUNDING LEGEND

This invention was made with government support under DK063430 awarded by the NIH. The government has certain rights in the invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a novel CD3 epsilon peptides, antibodies against the CD3 epsilon peptides and diagnostic kits for detecting CD3 epsilon peptides.

SEQUENCE LISTING

The instant application contains a Sequence Listing which has been submitted in ASCII format via EFS-Web and is hereby incorporated by reference in its entirety. Said ASCII copy, created on Apr. 11, 2011, is named 43092272.txt and is 4,177 bytes in size.

BACKGROUND OF THE INVENTION

SCID (severe combined immunodeficiency) presents one of the greatest opportunities for newborn screening (NBS), and also one of its most difficult challenges. This is the first condition detectable by NBS for which a cure is available, when identified and treated in early infancy (Railey et al., J Peds 2009; 155(6):834-40). However, the only test currently available with the potential of detecting SCID in the Guthrie specimen is the TREC (T-cell recombinant excision circle) assay (Chan & Puck, J Allergy Clin Immunol 2005; 115:391-8). The TREC assay presents technical challenges in that it is a primary screening assay using DNA, a protocol not accepted universally by the screening community (Green & Pass, Nat Rev Genet 2005; 6:147-55). Alternatively, immunoassays are used routinely in NBS as a first-tier screening protocol (Moyer et al., Hastings Cent Rep 2008; 38(3):32-39).

SCID (severe combined immunodeficiency) fulfills the requirements for a newborn screening (NBS) condition: sufficient prevalence (estimated at 1:50000 to 1:100000); biomarkers in the Guthrie specimen; and the availability of an appropriate therapy (bone marrow transplant). An assay to identify SCID and other T-cell deficiencies through quantification of T-cell recombinant excision circles (TRECs) has already been developed and is currently being used in pilot studies in Wisconsin and Massachusetts. In those two states, nearly 200,000 newborns have been screened without a SCID baby having been found, but other T-cell immunodeficiencies were identified in the screening. Because the TREC assay utilizes DNA technology, those laboratories with little experience, equipment or personnel in molecular biology may face challenges not encountered with an immunoassay. There exists a need for an alternative test for identifying alternate T-cell immunodeficiencies as well as alternate diagnostic kits.

SCID may result from a severe defect in both the T & B lymphocyte systems that leads to their diminishing. The absence of T-cells may be a defining characteristic of SCID and of other T-cell immunodeficiencies. (Edgar, J Clin Pathol 2008; 61:988-93). Because CD3 is part of the T-cell receptor complex on mature T-cells, it can be used as a marker for deficiency of T-cells (Dava, Immunol Rev. 2009; 232:22-33). Two case reports of CD3 deficiency causing immunodeficiency have been reported (Roberts et al., Blood 2007; 109: 3198-3206, Rieux-Laucat et al., N Engl J. Med. 206; 354: 1913-21). CD45, a common antigen present on all differentiated lymphocytes, provides an internal control for the assay. (Eley, Curr Allergy and Clin Immunol. March 2008:21:1-24).

Citation or identification of any document in this application is not an admission that such document is available as prior art to the present invention.

SUMMARY OF THE INVENTION

The present invention relates to, in part, Applicants' development of novel CD3 epsilon peptides, antibodies against the novel CD3 epsilon peptides. The antibodies of the present invention may be used to identify a CD3 deficiency in newborns.

In one embodiment, the invention pertains to an isolated CD3 epsilon peptide, in particular CD3 epsilon peptides which may comprise, consist essentially of or consist of residues 8-12 of SEQ ID NO: 1 or residues 6-10 of SEQ ID NO: 2. The invention also pertains to isolated antibodies against CD3 epsilon peptides, in particular CD3 epsilon peptides which may comprise, consist essentially of or consist of residues 8-12 of SEQ ID NO: 1 or residues 6-10 of SEQ ID NO: 2.

In another embodiment, the invention relates to a method of identifying an immunodeficiency in a patient, comprising isolating a blood sample from the patient and performing an immunoassay on the blood sample with an antibody against CD3 epsilon peptides, in particular CD3 epsilon peptides which may comprise, consist essentially of or consist of residues 8-12 of SEQ ID NO: 1 or residues 6-10 of SEQ ID NO: 2. In an advantageous embodiment, the immunodeficiency is severe combined immunodeficiency (SCID) or a T cell immunodeficiency.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts the amino acids CD3 epsilon peptides SEQ ID NOS: 1 and 2;

FIG. 3 depicts TREC tested specimens and controls;

FIG. 4 depicts decoded TREC tested specimens;

FIGS. 5A and 5B depict an average calculated percent of original peptide signal measured in Optical density by ELISA on Costar High binding plates coated at 10 μg/ml and the sequences in the left hand column of FIG. 5B correspond to SEQ ID NOS; 1 and 3-14 (from top to bottom) and the sequences in the right hand column of FIG. 5B correspond to SEQ ID NOS; 2 and 15-24 (from top to bottom);

FIG. 8 depicts MFI and calculated concentrations of T cells for The Danish National Newborn Screening Biobank specimens, positive for T cell deficiencies.

DETAILED DESCRIPTION

Figure 2:
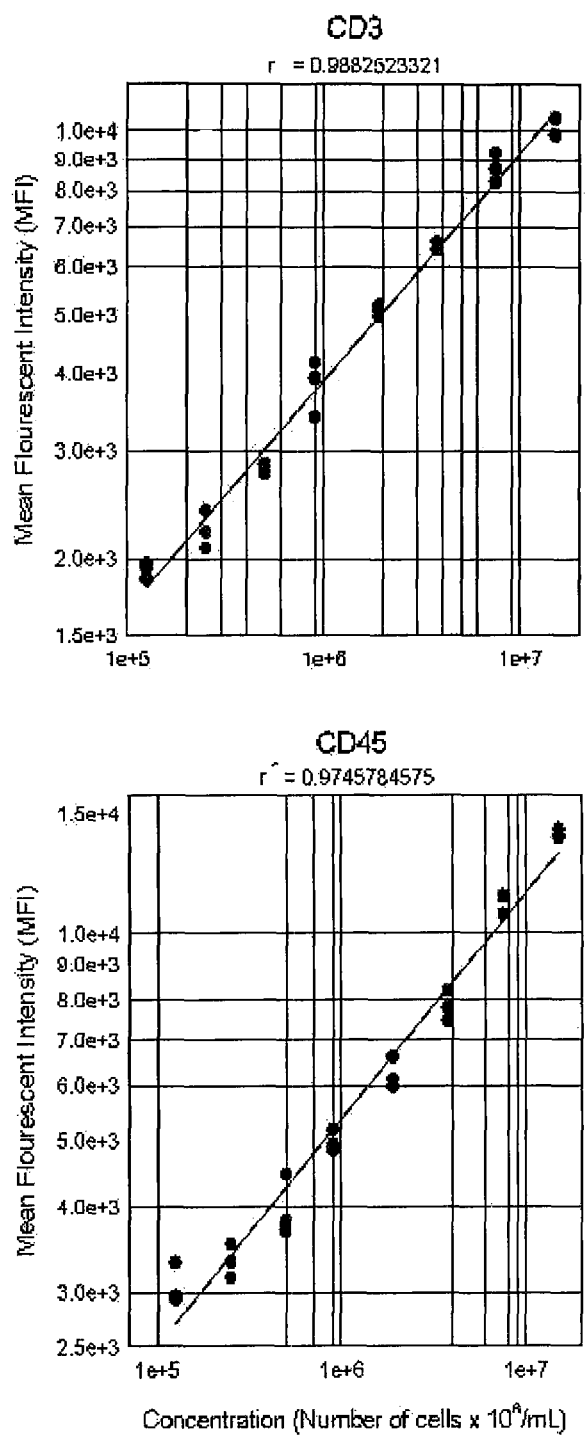
FIG. 2 depicts calibration curves for CD3 and CD45 quantification in dry blood spots (DBS)

The present invention relates to novel peptides that would not produce high affinity IgG antibody in mammalian hosts. In particular, the invention relates to novel peptide sequences derived from chicken and human CD3 epsilon which would elicit not only an immune response but would also allow for the development of high affinity IgY:

```
1) AKAKPVTRGAGA (12AA)      (SEQ ID NO: 1)

2) LYSGLNQRRI (10AA)        (SEQ ID NO: 2)
```

The present invention also relates to novel peptide sequences that comprise, consist essentially of or consist of residues 8-12 of SEQ ID NO: 1 or residues 6-10 of SEQ ID NO: 2.

The peptides of the present invention may also be useful for methods such as, but not limited to, ELISA, estimation of CD3+ cell counts, research, diagnosis, intracellular staining. The present invention relates to the production of chicken antibodies, in particular, chicken antibodies derived from SEQ ID NO: 1 and SEQ ID NO: 2 and/or peptides that comprise, consist essentially of or consist of residues 8-12 of SEQ ID NO: 1 or residues 6-10 of SEQ ID NO: 2. Biologically, IgG antibodies have 3 binding regions. Two regions are used to bind antigen (foreign debris or in this case CD3ε) and the third is used to bind different receptors for host biological functions. This can cause a problem with high background when using antibodies from other mammals to try and detect proteins from humans. This is not the case with chicken antibodies. Chicken antibodies function the same as all the other IgG's, however, the third region on the IgY is not active in humans, therefore background will be much lower compared to antibodies produced in other animals.

Laying hens are highly cost-effective as producers of antibodies compared with other mammals traditionally used for such production. Also chicken antibodies have biochemical advantages over mammalian antibodies due to the phylogenetical differences between avian and mammalian species, resulting in increased sensitivity as well as decreased background in immunological assays. In contrast to mammalian antibodies, chicken antibodies do not activate the human complement system nor will they react with rheumatoid factors, human anti-mouse IgG antibodies, or bacterial and human Fc receptors. Thus chicken antibodies offer many advantages over mammalian antibodies and are, even now, beginning to replace conventional sources of custom produced antibodies (see, e.g., http://www.oramune.com/custom.aspx?id=7).

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

As used herein, the term "antigen" or "immunogen" means a substance that induces a specific immune response in a host animal. The antigen may comprise a whole organism, killed, attenuated or live; a subunit or portion of an organism; a recombinant vector containing an insert expressing an epitope, polypeptide, peptide, protein, or fragment thereof with immunogenic properties; a piece or fragment of nucleic acid capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant The term epitope, also known as antigenic determinant, is the part of a macromolecule recognized by the immune system and able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term epitope is the part of a macromolecule recognized by the immune system and able to induce an immune reaction of the humoral type (B cells) and/or cellular type (T cells) The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The term"immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of T. parva are fully described in the PCT Application Serial No. PCT/US2004/022605 incorporated herein by reference in its entirety.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, preferably at least about 5 amino acids, more preferably at least about 10-15 amino acids, and most preferably about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of a CD3 epsilon protein or polyprotein. A polynucleotide encoding a fragment of the total protein or polyprotein, more advantageously, comprises or consists essentially of or consists of a minimum of 15 nucleotides, advantageously about 30-45 nucleotides, and preferably about 45-75, at least 57, 87 or 150 consecutive or contiguous nucleotides of the sequence encoding the total protein or polyprotein. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999), and in PCT Application Serial No. PCT/US2004/022605 all of which are incorporated herein by reference in their entireties can be used in the practice of the invention, without undue experimentation. Other documents cited and incorporated herein may also be consulted for methods for determining epitopes of an immunogen or antigen and thus nucleic acid molecules that encode such epitopes.

A "polynucleotide" is a polymeric form of nucleotides of any length, that contains deoxyribonucleotides, ribonucleotides, and analogs in any combination. Polynucleotides may have three-dimensional structure, and may perform any function, known or unknown. The term "polynucleotide" includes double-, single-stranded, and triple-stranded helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The term "codon optimization" refers to the process of optimally configuring the nucleic acid sequence encoding a protein, polypeptide, antigen, epitope, domain or fragment for expression/translation in selected host. In general, gene expression levels depend on many factors, such as promoter sequences and regulatory elements. One of the most important factors is the adaptation of the codon usage of the transcript gene to the typical codon usage of the host (Lithwich, G. and Margalit, H., Genome Res. 13, 2665-2673, 2003).

Therefore, highly expressed genes in prokaryotic genomes under translational selection have a pronounced codon usage bias. This is because they use a small subset of codons that are recognized by the most abundant tRNA species (Ikemura, T., J. Mol. Biol. 151, 389-409, 1981). The force that modulates this codon adaptation is called translational selection and its strength is important in fast-growing bacteria (Rocha, E. P., Genome Res. 14, 2279-2286, 2004; Sharp, P. M. et al., Nucleic Acids Res. 33, 1141-1153)). If a gene contains codons that are rarely used by the host, its expression level will not be maximal. This may be one of the limitations of heterologous protein expression (Gustafsson, C. et al., Trends Biotechnol. 22, 346-353, 2004) and the development of DNA vaccines (Ivory, C. and Chadee, K., Genet. Vaccines Ther. 2, 17, 2004). A high number of synthetic genes have been re-designed to increase their expression level. The Synthetic Gene Database (SGDB) (Wu, G. et al., Nucleic Acids Res. 35, D76-D79, 2007) contains information from more than 200 published experiments on synthetic genes. In the design process of a nucleic acid sequence that will be inserted into a new host to express a certain protein in optimal amounts, codon usage optimization is usually one of the first steps (Gustafsson, C., Trends Biotechnol. 22, 346-353, 2004). Codon usage optimization basically involves altering the rare codons in the target gene so that they more closely reflect the codon usage of the host without modifying the amino acid sequence of the encoded protein (Gustafsson, C., Trends Biotechnol. 22, 346-353, 2004). The information usually used for the optimization process is therefore the DNA or protein sequence to be optimized and a codon usage table (reference set) of the host.

There are several public web servers and stand-alone applications that allow some kind of codon optimization by anyone skilled in the art. 'GeneDesign' (Richardson, S. M. et al., Genome Res. 16, 550-556, 2006), 'Synthetic Gene Designer' (Wu, G. et al., Protein Expr. Purif. 47, 441-445, 2006) and 'Gene Designer' (Villalobos, A. et al., BMC Bioinformatics 7, 285, 2006) are packages that provide a platform for synthetic gene design, including a codon optimization step. With regard to the methods for codon usage optimization available in each server or program, the first programs developed used only the 'one amino acid—one codon' approach. More recent programs and servers now include further methods to create some codon usage variability. This variability reflects the codon usage variability of natural highly expressed genes and enables additional criteria to be introduced (such as the avoidance of restriction sites) in the optimization process. Most applications and web servers described herein provide three methods of codon optimization: a complete optimization of all codons, an optimization based on the relative codon usage frequencies of the reference set that uses a Monte Carlo approach and a novel approach designed to maximize the optimization with the minimum changes between the query and optimized sequences.

The following are non-limiting examples of polynucleotides: a gene or gene fragment, exons, introns, mRNA, tRNA, rRNA, siRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The invention further comprises a complementary strand to a polynucleotide encoding a CD3 epsilon protein, antigen, epitope or immunogen. The complementary strand can be polymeric and of any length, and can contain deoxyribonucleotides, ribonucleotides, and analogs in any combination thereof.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% or at least 95% free of these materials.

Hybridization reactions can be performed under conditions of different "stringency." Conditions that increase stringency of a hybridization reaction are well known. See for example, "Molecular Cloning: A Laboratory Manual", second edition (Sambrook et al., 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the CD3 epsilon polypeptides and functionally equivalent fragments thereof that may enhance, decrease or not significantly affect inherent properties of the polypeptides encoded thereby. These functionally equivalent variants, derivatives, and fragments display the ability to retain CD3 epsilon activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the CD3 epsilon polynucleotide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin et al., 1990 modified as in Karlin et al., 1993.

Another example of a mathematical algorithm used for comparison of sequences is the algorithm of Myers et al., 1988. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson et al., 1988.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul et al., 1996; Altschul et al., 1990; Gish et al., 1993; Karlin et al., 1993; all of which are incorporated by reference herein).

In general, comparison of amino acid sequences is accomplished by aligning an amino acid sequence of a polypeptide of a known structure with the amino acid sequence of a polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA. 1983 February; 80(3):726-30, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Vector NTI Software™, Invitrogen Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

And, without undue experimentation, the skilled artisan can consult with many other programs or references for determining percent homology.

The invention further encompasses the CD3 epsilon polynucleotides contained in a vector molecule or an expression vector and operably linked to a promoter element and optionally to an enhancer.

A "vector" refers to a recombinant DNA or RNA plasmid, bacteriophage, or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes vectors for cloning as well as viral vectors.

The term "recombinant" means a polynucleotide of semi-synthetic, or synthetic origin that either does not occur in nature or is linked to another polynucleotide in an arrangement not found in nature.

"Heterologous" means derived from a genetically distinct entity from the rest of the entity to which it is being compared. For example, a polynucleotide, may be incorporated by genetic engineering techniques into a plasmid or vector derived from a different source, and is thus a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a CD3 epsilon polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. a CD3 epsilon peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450; 6,312,683, and 6,596,279; U.S. patent application Serial No. 920,197, filed Oct. 16, 1986; WO 90/01543; WO91/11525; WO 94/16716; WO 96/39491; WO 98/33510; EP 265785; EP 0 370 573; Andreansky et al., 1996; Ballay et al., 1993; Feigner et al., 1994; Frolov et al., 1996; Graham, 1990; Grunhaus et al., 1992; Ju et al., 1998; Kitson et al., 1991; McClements et al., 1996; Moss, 1996; Paoletti, 1996; Pennock et al., 1984; Richardson (Ed), 1995; Smith et al., 1983; Robertson et al., 1996; Robinson et al., 1997; and Roizman, 1996. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-CD3 epsilon peptides or fragments thereof to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of CD3 epsilon polypeptides, antigens, epitopes or immunogens. Advantageously, the vector contains and expresses a polynucleotide that includes, consists essentially of, or consists of a polynucleotide coding for (and advantageously expressing) a CD3 epsilon antigen, epitope or immunogen, in a pharmaceutically acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a CD3 epsilon polypeptide, antigen, epitope or immunogen (e.g., hemagglutinin, neuraminidase, nucleoprotein) or a fragment thereof.

According to another embodiment, the vector or vectors in the preparation comprise, or consist essentially of, or consist of polynucleotide(s) encoding one or more proteins or fragment(s) thereof of a CD3 epsilon polypeptide, antigen, epitope or immunogen, the vector or vectors expressing the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different CD3 epsilon isolates encoding the same proteins and/or for different proteins, but advantageously the same proteins. Preparations containing one or more vectors containing, consisting essentially of or consisting of polynucleotides encoding, and advantageously expressing, advantageously in vivo, a CD3 epsilon polypeptide, antigen, fusion protein or an epitope thereof. The invention is also directed at mixtures of vectors that contain, consist essentially of, or consist of coding for, and express, different CD3 epsilon proteins, polypeptides, antigens, epitopes or immunogens, e.g., a D3 epsilon polypeptide, antigen, epitope or immunogen from different species such as, but not limited to, humans, horses, pigs, seals, whales, in addition to avian species including chicken, turkeys, ducks and geese.

The term plasmid covers any DNA transcription unit comprising a polynucleotide according to the invention and the elements necessary for its in vivo expression in a cell or cells of the desired host or target; and, in this regard, it is noted that a supercoiled plasmid and all of its topoisomers, open-circular plasmid, as well as linear forms of the plasmid, are intended to be within the scope of the invention.

Each plasmid comprises or contains or consists essentially of, in addition to the heterologous polynucleotide encoding a recombinant protein, antigen, epitope or immunogen, optionally fused with a polynucleotide encoding an heterologous peptide sequence, variant, analog or fragment, operably linked to a promoter or under the control of a promoter or dependent upon a promoter. In general, it is advantageous to employ a strong promoter that is functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter segment, which may or may not be associated with the enhancer segment. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter is either of a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β13-globin gene (van Ooyen et al., 1979).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Advantageous host cells include, but are not limited to, baby hamster kidney (BHK) cells, colon carcinoma (Caco-2) cells, COST cells, MCF-7 cells, MCF-10A cells, Madin-Darby canine kidney (MDCK) lines, mink lung (Mv1Lu) cells, MRC-5 cells, U937 cells and VERO cells. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of a protein, antigen, epitope or immunogen in a target cell. Determination of the therapeutically effective amount is routine experimentation for one of ordinary skill in the art. In one embodiment, the formulation comprises an expression vector comprising a polynucleotide that expresses a CD3 epsilon antigen, epitope or immunogen and a pharmaceutically acceptable carrier, vehicle or excipient. In an advantageous embodiment, the pharmaceutically acceptable carrier, vehicle or excipient facilitates transfection and/or improves preservation of the vector or protein.

The pharmaceutically acceptable carriers or vehicles or excipients are well known to one skilled in the art. For example, a pharmaceutically acceptable carrier or vehicle or excipient can be sterile water, a 0.9% NaCl (e.g., saline) solution or a phosphate buffer. Other pharmaceutically acceptable carriers or vehicles or excipients that can be used for methods of this invention include, but are not limited to, poly-(L-glutamate) or polyvinylpyrrolidone. The pharmaceutically acceptable carriers or vehicles or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The present invention also encompasses methods for making antibodies. In an advantageous embodiment, the antibodies are chicken antibodies. In a particularly advantageous embodiment, the antibodies are isolated from the yolk of eggs laid by immunized hens. A laying hen produces approximately five to six eggs per week with a yolk volume of approximately 15 ml per egg, the antibody concentration of which is comparable to that of serum. Therefore, in one week a hen produces egg antibodies equivalent to 75 to 90 ml of serum or 150 to 180 ml of whole blood. This could be compared to an immunized rabbit, which yields approximately 20 ml whole blood per week. Only large mammals such as cows or horses can produce more antibodies than a laying hen. The blood collection procedure is time consuming and stressful for the animal. Furthermore, the cost of feeding and handling is considerably lower for a hen than for a rabbit. Crude egg yolk may be used as an antibody source, but the lipids in the yolk may interfere with the antibody activity. Therefore, avian antibodies may be purified from the yolk prior to use.

To stimulate the immune response of experimental animals, the desired antigen is applied in combination with various adjuvant compounds (Hilgers et al. 1998, Vet. Immunol. Immunopathol. 66 159-171). Using these compounds, antigen is appropriately presented, e.g. in the form of an emulsion, to the organism and the immune system non-specifically stimulated to produce antibodies by additional components (e.g. adamantyldipeptide, inactivated microorganisms or their parts). Of tested adjuvant preparations the best results were obtained with emulsions of antigens in mineral oil mixed with complete Freund's adjuvant for the first injection and with incomplete Freund's for boosters. Similar immune responses were found when only solutions of antigens in PBS were used for injections (Svendsen-Bollen et al. 1996, J. Immunol. Methods 191 113-120, Schwarzkopf & Thiele 1996, ALTEX 13 (Suppl. 96), 22-25). Just recently, application of lipid nanoparticles causing only minor tissue irritation at the injection sites, appears to be a promising alternative to complete Freund's adjuvant (Olbrich et al. 2002, ATLA 30 443-458).

In respect to antibody titers it is hard to judge which organism, the rabbit or the chicken, is superior for antibody production. Even when the experimental conditions are kept to be the same for both animal species the titers depend on the antigen immunogenicity for the animal used. For example, the chicken is able to produce antibodies against one serotype of rotavirus with a neutralization titer more than 4 times higher than that derived from rabbit blood. On the other hand, for another serotype chicken antibodies show lower activity than rabbit antisera (Hatta et al. 1993, Biosci. Biotech. Biochem. 57 450-454). Thanks to the evolutionary distance between birds and mammals, the chicken is superior for the production of antibodies against conserved mammalian antigens, which are hardly immunogenic for experimental mammals. Chicken IgY is usually produced against a greater number of antigenic epitopes on a mammalian antigen thus giving an amplified signal and greater test sensitivity. Another advantage lies in the possibility of developing high titer chicken antibodies even though low doses of mammalian antigen (0.001-0.01 mg/dose) are applied (Gassmann et al. 1990, FASEB J. 4 2528-2532, Larsson et al. 1998, Food Agric. Immunol. 10 29-36, Knecht et al. 1996, Eur. J. Biochem. 236 609-613).

So far, the major limitation preventing a wide application of IgYs lies most probably in their purification from egg yolks. It is true that a procedure as simple as the preparation of antisera from mammalian blood is not available for chicken antibodies. IgY comprises about 5% of egg yolk proteins dispersed in yolk lipid emulsion together with lipoproteins and glycoproteins (Juneja & Kim, 1997, Hen Eggs: Their Basic and Applied Science pp. 57-72 eds T Yamamoto, L R Juneja, H Hatta and M Kim (USA: CRC Press)). There are plenty of different procedures developed for IgY purification (Hodek et al. 1998, CZ Patent 281298, Stalberg et al. 2001, De Meulenaer & Huyghebaert 2001). The first step of these procedures (after yolk separation) is always based on removal of the lipid fraction by its extraction into organic solvent, precipitation using freezing or precipitation agents or hydrophobic chromatography. Recently, the use of an aqueous two-phase system with phosphate and Triton X-100 separation of lipids and watersoluble proteins (IgY fraction) has been introduced (Stalberg et al. 2001, Ups. J. Med. Sci 0.106 99-110). The resulting water-soluble protein fraction is usually separated by fraction precipitation or chromatography on ion-exchange, thiophilic or size-exclusion columns (Polson et al. 1980, Immunol. Commun. 9 495-514, Bade & Stegemann 1984, J. Immunol. Methods 72 421-426, Hassl & Aspock 1988, J. Immunol. Methods 110 225-228, Hatta et al. 1990, Agric. Biol. Chem. 54 2531-2535, Akita & Nakai 1993, J. Immunol. Methods 160 207-214, Schwarzkopf & Thiele 1996, ALTEX 13 (Suppl. 96), 22-25, Cook et al. 2001, J. Biosci. Bioeng. 91 305-310).

Interestingly, chicken antibodies were efficiently captured from crude samples on an affinity column with immobilized synthetic ligand for immunoglobulins. Using this technique in a single purification step the purity of IgY higher than 90% was obtained (Verdoliva et al. 2000, J. Chromatogr. 749 233-242). The majority of protocols, however, apply 2-3 purification steps to obtain a final preparation of a high purity (98%), yielding 70-100 mg IgY per yolk. To prepare monospecific antibodies, an affinity chromatography technique on immobilized antigen is usually exploited. Specifically bound IgY is eluted by strong acidic or basic buffers (Ntakarutimana et al. 1992, J. Immunol. Methods 153 133-140, Kuronen et al. 1997, Eur. J. Clin. Chem. Clin. Biochem. 35 435-440, Tini et al. 2002, Comp. Biochem. Physiol. A Mol. Integr. Physiol. 31 569-574). Purified IgYs show high stability when they are stored at 4° C. They have retained their activity for more than 10 years (Larsson et al. 1999, Food Agric. Immunol. 11 43-49).

Chloroform/PEG extraction may be performed on yolks for IgY purification, after which the IgY may be further manipulated to enrich for the Peptide specific IgY.

The present invention also encompasses methods for diagnostic and genetic analysis of SCID markers, such as CD3 and CD45. In an advantageous embodiment, the analysis may comprise the steps of constructing an appropriately labeled beadset, exposing the headset to a clinical sample, and analyzing the combined sample/beadset by flow cytometry is disclosed. Flow cytometric measurements are used to classify, in real-time, beads within an exposed beadset and textual explanations, based on the accumulated data obtained during real-time analysis, are generated for the user.

One well known prior art technique used in assay procedures for which a multiplexed assay capability would be particularly advantageous is flow cytometry. Flow cytometry is an optical technique that analyzes particular particles in a fluid mixture based on the particles' optical characteristics using an instrument known as a flow cytometer. Background information on flow cytometry may be found in Shapiro, "Practical Flow Cytometry," Third Ed. (Alan R. Liss, Inc. 1995); and Melamed et al., "Flow Cytometry and Sorting," Second Ed. (Wiley-Liss 1990), which are incorporated herein by reference. Flow cytometers hydrodynamically focus a fluid suspension of particles into a thin stream so that the particles flow down the stream in substantially single file and pass through an examination zone. A focused light beam, such as a laser beam illuminates the particles as they flow through the examination zone. Optical detectors within the flow cytometer measure certain characteristics of the light as it interacts with the particles. Commonly used flow cytometers such as the Becton-Dickinson Immunocytometry Systems "FACSCAN" (San Jose, Calif.) can measure forward light scatter (generally correlated with the refractive index and size of the particle being illuminated), side light scatter (generally correlated with the particle's size), and particle fluorescence at one or more wavelengths. (Fluorescence is typically imparted by incorporating, or attaching a fluorochrome within the particle.) Flow cytometers and various techniques for their use are described, generally, in "Practical Flow Cytometry" by Howard M. Shapiro (Alan R. Liss, Inc., 1985) and "Flow Cytometry and Sorting, Second Edition" edited by Melamed et al. (Wiley-Liss, 1990).

An important feature of the flow cytometric technology and techniques described here is the fabrication and use of particles (e.g., microspheres or beads that make up a headset). It is through the use of appropriately labeled homogeneous bead subsets, combined to produce a pooled beadset, that the instant multiplexed assay method is practiced. Beads suitable for use as a starting material in accordance with the invention are generally known in the art and may be obtained from manufacturers such as Luminex, Spherotech and Molecular Probes. Once a homogeneous subset of beads is obtained, the beads are labeled with an appropriate reactant such as a biomolecule (such as an antibody), DNA sequence, and/or other reactant. Known methods to incorporate such labels include polymerization, dissolving, and attachment.

Development of a multiplexed assay for use in accordance with the invention can be divided into three phases: (1) preprocessing, (2) real-time analysis, and (3) interpretation. During the preprocessing phase, baseline data is collected independently, via flow cytometric techniques, for each of an assay's bead subsets. Baseline data is used to generate a set of functions that can classify any individual bead as belonging to one of the assay's subsets or to a rejection class. During the analysis phase, flow cytometric measurements are used to classify, in real-time, each bead within an exposed beadset according to the aforementioned functions. Additionally, measurements relating to each subset's analyte are accumulated. During the interpretation phase the assay's real-time numerical results are associated with textual explanations and these textual explanations are displayed to a user. The inventive method allows the detection of a plurality of analytes simultaneously during a single flow cytometric processing step. Benefits of the inventive multiplex assay method include increased speed and reduced cost to analyze a clinical sample.

In particular, the assays developed by Luminex are particularly advantageous for the present invention, e.g., the disclosures of U.S. Pat. Nos. 7,645,868; 7,608,398; 7,551,763; 7,523,637; 7,505,131; 7,465,540; 7,455,980; 7,445,844; 7,385,053; 7,362,432; 7,318,336; 7,274,316; 7,267,798; 7,260,495; 7,244,570; 7,241,883; 7,234,853; 7,230,092; 7,226,737; 7,189,516; 7,141,431; 7,069,191; 7,047,138; 6,939,720; 6,916,661; 6,905,766; 6,773,812; 6,696,304; 6,696,265; 6,658,357; 6,649,414; 6,632,526; 6,599,331; 6,592,822; 6,528,165; 6,524,793; 6,514,295; 6,449,562; 6,411,904; 6,366,354; 6,268,222; 6,139,800; 6,057,107; 6,046,807; 5,981,180; 5,802,327 and 5,736,330.

The present invention also includes methods of analyzing and storing the diagnostic data of the present invention. The data stored in the database can be integrated with or compared to other data or databases with other SCID markers.

The present invention, therefore, encompasses computer-assisted methods for tracking SCID markers encompassing using a computer-based system comprising a programmed computer comprising a processor, a data storage system, an input device and an output device, and comprising the steps of generating a SCID profile by inputting into the programmed computer through the input device diagnostic data, inputting into the programmed computer through the input device diagnostic data, correlating the inputted data with a profile using the processor and the data storage system, and outputting a profile to the output device.

The databases and the analysis thereof will be accessible to those to whom access has been provided. Access can be provided through rights to access or by subscription to specific portions of the data. The data can be provided in any form such as by accessing a website, fax, email, mailed correspondence, automated telephone, or other methods for communication. These data can also be encoded on a portable storage device.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect and transmit the data to a data analysis module, a network interface for receiving data from the data analysis module, and optionally further adapted to combine multiple data from one or more individual patients, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual patients, and to transmit the data via a network to other sites, and/or a storage device. For example, the data collected by the data collection module leads to a determination of the absence or presence of a marker in a patient.

The invention further comprehends methods of doing business by providing access to such computer readable media and/or computer systems and/or data collected from patients to users; e.g., the media and/or sequence data can be accessible to a user, for instance on a subscription basis, via the Internet or a global communication/computer network; or, the computer system can be available to a user, on a subscription basis.

The invention will now be further described by way of the following non-limiting examples.

EXAMPLES

Example 1

Novel CD3 Epsilon (CD3ε) Peptides

The target protein chosen for these studies is human CD3 epsilon (CDR). It is very similar in the mammalian species that Applicants routinely use to produce antibodies (rabbit, mouse). Because of the high similarity between sequences it is unlikely that the animal would make a decent immunological response to immunizing peptides and would not produce high affinity IgG antibody. The sequence for chicken and human CD3 epsilon are known and have sufficient differences that allowed Applicants to determine 2 potential peptide sequences which would elicit not only an immune response but would also allow for the development of high affinity IgY:

```
1) AKAKPVTRGAGA (12AA)      (SEQ ID NO: 1)

2) LYSGLNQRRI (10AA)        (SEQ ID NO: 2)
```

Biologically, IgG antibodies have 3 binding regions. Two regions are used to bind antigen (foreign debris or in this case CD3ε) and the third is used to bind different internal receptors for host biological functions. This can cause a problem with high background when using antibodies from other mammals to try and detect proteins from humans. This is not the case with chicken antibodies. Chicken antibodies function the same as all the other IgG's, however, the third region on the IgY is not active in humans, therefore background will be much lower compared to antibodies produced in other animals.

Laying hens are highly cost-effective as producers of antibodies compared with other mammals traditionally used for such production. Also chicken antibodies have biochemical advantages over mammalian antibodies due to the phylogenetical differences between avian and mammalian species, resulting in increased sensitivity as well as decreased background in immunological assays. In contrast to mammalian antibodies, chicken antibodies do not activate the human complement system nor will they react with rheumatoid factors, human anti-mouse IgG antibodies, or bacterial and human Fc receptors. Thus chicken antibodies offer many advantages over mammalian antibodies and are, even now, beginning to replace conventional sources of custom produced antibodies (see, e.g., http://www.oramune.com/custom.aspx?id=7).

Example 2

A Multiplex Immunoassay for SCID using Guthrie Specimens

SCID (severe combined immunodeficiency) fulfills the requirements for a newborn screening (NBS) condition: sufficient prevalence (estimated at 1:50000 to 1:100000); biomarkers in the Guthrie specimen; and the availability of an appropriate therapy (bone marrow transplant). An assay to identify SCID and other T-cell deficiencies through quantification of T-cell recombinant excision circles (TRECs) has already been developed and is currently being used in pilot studies in Wisconsin and Massachusetts. In those two states, nearly 200,000 newborns have been screened without a SCID baby having been found, but other T-cell immunodeficiencies were identified in the screening. Because the TREC assay utilizes DNA technology, those laboratories with little experience, equipment or personnel in molecular biology may face challenges not encountered with an immunoassay. Applicants describe here an alternative test: a multiplex immunoassay that uses the Guthrie specimen, with CD3 as a marker for T-cells, and with CD45 as a marker for total lymphocytes.

Building on methods and techniques previously described by Applicants, Applicants have developed a two-plex assay that utilizes the multiplexing capability of the Luminex platform. To measure CD3 and CD45, Applicants developed an immunoassay that uses antibody pairs to both biomarkers. The assays for the two biomarker were developed separately, and then combined and optimized.

Calibrators were prepared to generate standard curves for CD3 and CD45. These standard curves demonstrate the excellent performance parameters of the antibodies and buffer. The multiplex assay was validated against eight coded specimens previously characterized by the New England Newborn Screening Program (NESP) laboratory for TREC quantity; five were from known SCID cases, and three were controls. All were correctly identified by Applicants' new CD345 assay.

Applicants' multiplex immunoassay, using CD3 and CD45 as biomarkers, shows concordance with the TREC assay in detecting immunodeficiency using the Guthrie specimen. Its performance characteristics—sensitivity, specificity, and low coefficient of variation are characteristic of an immunoassay. The assay holds promise as an alternative or complement to the TREC assay for detecting immunodeficies such as SCID. Inclusion in population-based pilot evaluations of SCID NBS is warranted.

SCID (severe combined immunodeficiency) presents one of the greatest opportunities for newborn screening (NBS), and also one of its most difficult challenges. This is the first condition detectable by NBS for which a cure is available, when identified and treated in early infancy (Railey et al., J Peds 2009; 155(6):834-40). However, the only test currently available with the potential of detecting SCID in the Guthrie specimen is the TREC (T-cell recombinant excision circle) assay (Chan & Puck, J Allergy Clin Immunol 2005; 115:391-8). The TREC assay presents technical challenges in that it is a primary screening assay using DNA, a protocol not accepted universally by the screening community (Green & Pass, Nat Rev Genet. 2005; 6:147-15).

Alternatively, immunoassays are used routinely in NBS as a first-tier screening protocol (Moyer et al., Hastings Cent Rep 2008; 38(3):32-39).

Applicants report here the technical feasibility of NBS for SCID by immunoassay, and the development and validation of a multiplex assay that simultaneously quantifies T-cells and total lymphocytes, in a 3-mm punch from a Guthrie specimen. The absence of T-cells is the defining characteristic of SCID and of other T-cell immunodeficiencies. (Edgar, J Clin Pathol 2008; 61:988-93) Because CD3 is part of the T-cell receptor complex on mature T-cells, it can be used as a marker for deficiency of T-cells (Dave, Immunol Rev. 2009; 232:22-33). Two case reports of CD3 deficiency causing immunodeficiency have been reported (Roberts et al., Blood 2007; 109:3198-3206, Rieux-Laucat et al., N Engl J. Med. 206; 354:1913-21). CD45, a common antigen present on all differentiated lymphocytes, provides an internal control for the assay. (Eley, Curr Allergy and Clin Immuna March 2008; 21:1-24) Using two different Luminex microsphere sets, Applicants developed separate assays for CD3 and CD45, and then combined these and optimized the duplex assay. Anti-CD3 specific monoclonal antibody (USBiological) was coupled to Luminex xMAP microspheres according to the instructions provided by Luminex (http//Luminexcorp.custhelp.com). Using techniques previously described (10), CD3 capture monoclonal antibody (25-100 μg) was coupled to $5\times10^6$ Luminex beads, region 32 (L-100-C132-04). Similarly, 25-100 μg of CD45 capture monoclonal (USBiological) was coupled to $5\times10^6$ Luminex beads, region 33 (L-100-C133-04). Equal volumes of the two coupled bead sets were mixed.

The anti-CD3 polyclonal and anti-CD45 monoclonal detector antibodies (USBiological) were biotinylated with a 20-fold molar excess of sulfo-NHS-LC-biotin (Pierce). The CD3 detection antibody was used at a 1:300 dilution, and the CD45 detection antibody was used at 2 μg/mL. Both capture and detector antibodies to CD45 were selected so that they recognized all CD45 isoforms. The performance of the antibodies was determined by titer studies that evaluated affinity and sensitivity, and by cross-reaction tests that evaluated their specificity. The concentration of each antibody was titrated so as to produce optimal performance. The two immunoassays were developed separately and optimized for affinity, sensitivity, and specificity; they were then combined into a duplex format.

T-cells and total lymphocytes were counted in whole blood (Tennessee Blood) by flow cytometry; leukocyte-reduced blood (Tennessee Blood) was examined by flow cytometry to confirm absence of CD3 and CD45. The leukocyte-reduced blood was washed four times with PBS, and the resulting packed red blood cells were stored at −80° C. Leukocytes were collected from the whole blood by use of Histopaque 1077 (Sigma) according to the manufacturer's instructions, counted on a hemacytometer, and resuspended at a concentration of $30\times10^6$ cells/mL in human serum (BioResource Technology) containing 2% protease inhibitor cocktail (Sigma-Aldrich). Doubling dilutions were carried out to achieve a final leukocyte concentration of $0.25\times10^6$/mL. An equal volume of packed red blood cells was added to each dilution. Leukocyte enriched blood (75 μL) was spotted on Ahlstrom Grade 226 specimen collection paper and left to dry overnight. Dried spots were wrapped in foil and stored in a sealable bag with desiccant at −20° C. Controls were made from whole adult blood, with lymphocytes previously measured by flow cytometry.

The assay buffer was prepared using PBS (pH 7.4), 0.055% Tween 20, 0.05% sodium azide, and 0.2% gelatin. To make the elution buffer, 1% protease inhibitor cocktail (Sigma) and Triton-X 114 (0.1%) were added to the assay buffer. A single 3-mm punch from a standard, control, or Guthrie specimen was placed in an individual well of a microtiter plate and eluted overnight at room temperature in 100 μL of elution buffer with gentle shaking For the assay, 75 μL of the specimen eluate were added to 50 μL of the CD3 and CD45 bead mix, to yield 3000 microspheres per well. After 3 hr incubation with the capture antibodies at 37° C. and gentle shaking, microspheres were washed three times in 100 μL of assay buffer. Next, 50 μL of the anti-CD3 and anti-CD45 detector antibody mixture were added to each well. The microplates were incubated for 1 hr at 37° C. with gentle shaking, and the microspheres were again washed three times with 100 μL of assay buffer. For detection signal, 50 μL of streptavidin phycoerythrin (Prozyme) was added at 4 μg/mL and incubated for 20 minutes at 37° C. The microspheres were aspirated, washed three times in 100 μL of assay buffer, re-suspended in 50 μL of 0.2 μg/mL anti-phycoerythrin (Biolegend), and incubated for 30 minutes at 37° C. with gentle shaking. Microspheres were washed three times in 100 μL of assay buffer, resuspended in 50 μL of 4 μg/mL streptavidin phycoerythrin, and incubated at 37° C. for 20 minutes with gentle shaking Microspheres were aspirated, washed three times with 100 μL of assay buffer, and then resuspended in 110 μL of Luminex sheath fluid, for analysis.

Data collection and analysis were performed in multiplex acquisition mode on the Luminex 100 instrument. Luminex software (LX100 IS 2.3) calculated the results, expressed as median fluorescence intensity (MFI) of 100 microspheres of each set. The software LiquiChip Analyser 1.0 (Qiagen) was used to analyze the raw data. All control Guthrie specimens were provided by the New York State Department of Health Newborn Screening Program. In compliance with IRB (Institutional Review Board) guidance, no identifying information was transferred with the specimens.

Calibration curves for CD3 and CD45 quantification in dry blood spots (DBS) are shown in FIG. 2. The analytical limit of detection was determined using the mean plus 3 SD, from 12 replicates of the zero calibrator. The analytical detection limit in DBS samples for CD3 was $0.25 \times 10^6$ cells/mL, and it was $0.125 \times 10^6$ cells/mL for CD45. Accuracy of the immunoassay was determined with DBS sample controls made from blood in which lymphocytes had previously been quantified by flow cytometry. No crossreactivity was observed between CD3 and CD45 antibodies in the duplex format. Using the mean of 12 independent measurements for each concentration of calibrators, Applicants examined the assay precision profiles. Applicants found that the CVs were approximately 10% for the lower concentrations of CD3, and 12% for the lower concentrations of CD45. At all concentrations, the inter-assay CV was 3% for CD3, and 1% for CD45. The intraassay CVs for CD3 ranged from 3% to 11% and for CD45 from 1% to 12%.

Guthrie specimens from randomly chosen newborns, normal-weight newborns (>2000 g), and low-birth weight newborns (>500 g-2000 g) were tested to determine a range for CD3 and CD45. A total of 49 Guthrie specimens were tested: 29 random newborns, 10 normal-birth weight newborns, and 10 low-birth weight newborns. To determine T-cell counts, Applicants tested NBS specimens in duplicate in three separate experiments, using the calibrators described above. Counts ranged from 1 to $13 \times 10^6$/mL cells CD3 and from 2.1 to $34 \times 10^6$/mL cells CD45. Specimens from low-birth weight newborns showed a range from 1.5 to $9.1 \times 10^6$/mL cells for CD3, and from 0.5 to $9.7 \times 10^6$/mL cells for CD45 (FIGS. 3 and 4).

The coded punches from New England Newborn Screening Program were tested as singlicates, due to the scarcity of these positive specimens. A set of duplicate random Guthrie specimens was added to the same plate. A reading of "Low" by the software indicates that the value of the marker is too low to compute; likewise a report of "High" denotes that the value is above the highest standard. The eight coded specimens were classified as positive or negative by the CD345 assay and these results were decoded (FIG. 4). Five of the eight 3-mm punches had tested Low/Absent for TRECs, and the remaining three (including one from an adult) were controls. All results from the CD345 assay were concordant with results from the TREC assay (FIG. 4).

The medical and scientific literature is replete with reports of successful cures for SCID (Railey et al., J Peds 2009; 155(6):834-40, Griffith et al., J Allergy Clin Immunol. 2008; 122(6):1087-96. Finlayson, Curr allergy and Clin Immunol 2008:21:19-24, Buckley, J Allergy Clin Immunol 2004; 113 (4):793-800), thus making it a prime candidate for addition to NBS panels. Currently, the DNA-based TREC assay is the only assay that has been shown to detect lymphopenia in the Guthrie specimen (Puck, J Allergy Clin Immunol. 2007; 120: 760-8). Here, Applicants report an alternative, an immunoassay using two T-cell markers that was able to differentiate immunodeficient newborns from controls.

This is the first description of the use of CD3 as a biomarker for lymphopenia in an immunoassay of Guthrie specimens, although two CD3-deficient cases have been documented in the literature (Roberts et al., Blood 2007; 109:3198-3206, Routes et al., JAMA 2009; 302:2465-70). The CD45 biomarker provides an internal control for assay performance and for the actual presence of a punched sample in each well. It is important to note that the values for CD3 in control and affected infants differed by 10-fold, thereby assuring adequate separation between these two values for other lymphopenias that might be identified as assay validation continues. Given the limited number of positive specimens that were available for evaluation, it is impossible at this time to establish a cutoff for CD3. As discussed recently, other T-cell immunodeficiencies can be detected by screening with TRECs (Routes et al., JAMA 2009; 302:2465-70). Applicants believe that the CD345 immunoassay described here has comparable potential once it has undergone further evaluation with positive specimens.

Applicants' CD345 multiplex assay demonstrated concordance of a TREC analysis on Guthrie specimens, and thus holds comparable potential as a complement, or substitute, for the TREC assay. Importantly, its multiplex format will allow the incorporation of additional markers for SCID into the panel in the future, to improve the specificity, and perhaps also to classify other immunodeficiencies. Additionally, analysis of the punches used for CD345 elution assay (ghosts) in the TREC assay provided concordant results with her first TREC testing. This reusable quality of the CD345 test materials validates their use as a primary screen followed by the TREC as a confirmatory test.

These preliminary data demonstrate that the clinical validity of the CD3-45 multiplex immunoassay is similar to that achievable with the TREC assay. The performance characteristics warrant the assay's inclusion in population-based evaluations.

Example 3

Results of CD3 Epsilon (CD3ε) Peptide Variants Produced by Systematic Single Residue Sequential Replacement Tested in CD3ε ELISA The capture antibody of the CDR assay was produce by inoculation with 2 peptides. The sequence of these two peptides is AKAKPVTRGAGA (SEQ ID NO: 1) and LYSGLN-QRRI (SEQ ID NO: 2) respectively. To determine the key immune-dominate region of the peptide, 12 variants of original peptide 1 (SEQ ID NO: 1) and 10 variants of original peptide 2 (SEQ ID NO: 2) were made with alanine substitution (or valine when alanine is the original amino acid). These were produced by GenScript, shipped, in solid form, at room temperature, to our lab and were dissolved in 1 ml of 0.05 TBS buffer.

Single peptides were coated on to Costar high binding 96 well plates at a concentration of 10 μg and 2 μg in 0.05 TBS buffer pH 7.4 in quadruplicate and tested in an alkaline phoshotase based ELISA. Plate blanks were subtracted from the optical densities obtained for each peptide. The peptides are compared to the original by percent of original signal. As noted in Table 1 the twelfth substitution was both an alanine at position twelve and a glutamic acid for threonine at position seven. This was an inadvertent oversight by the manufacturer.

Figure 5A:
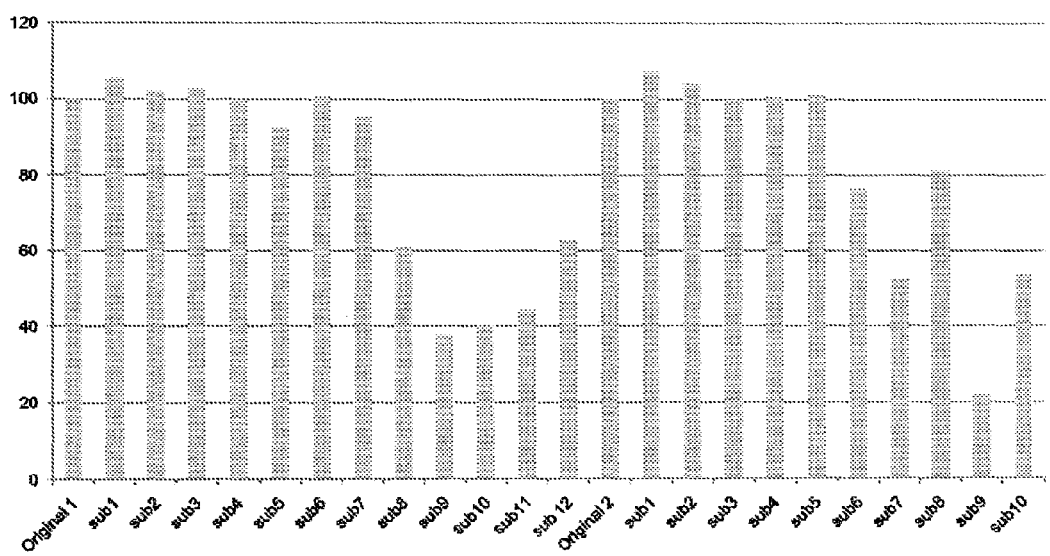

The results of these experiments are demonstrated in FIGS. 5A and 5B. The substitution of alanine for residues 8-12 results in 38 to 63% reduction in signal vs. the original peptide 1 (SEQ ID NO: 1) and for residues 6-10 in original peptide 2 (SEQ ID NO: 2) displayed a 22 to 81% reduction in signal for plates coated at 10 μg/ml. The results from using a coating concentration of 2 μg/ml were similar. These experiments show that a small change in the peptide sequence will greatly reduce the affinity with which the anti-human CD38 detection antibody can bind with its recognized epitope.

The OD for original peptide 1 (SEQ ID NO: 1) was 1.5 and peptide 2 (SEQ ID NO: 2) elicited a signal of 1.0 when tested under the same conditions. This trend was observed in the three separate experiments and the conclusion reached is that original peptide 1 (SEQ ID NO: 1) generated an antibody with a greater affinity for peptide 1 than the antibody against peptide 2 (SEQ ID NO: 2).

Example 4

An Improved Immunoassay for the Detection of Severe Combined Immunodeficiency in Newborn Dry Blood Spots Applicants previously reported a bead array based multiplex immunoassay for the detection of human CD3 and all isoforms of human CD45 from Guthrie specimens. Applicants demonstrated that CD3 could be used as an indication of T cell deficiencies, such as severe combined immunodeficiency (SCID), in a 3 mm punch of new born dry blood. Here Applicants report changes to the assay that greatly improve its performance and extend its validation.

An antibody pair was used to capture and detect CD3. Applicants replaced the previously used commercial detection antibody with a custom designed detection antibody. Assay performance was evaluated and compared with previous results. Validation of the assay was done with one hundred twenty four coded 3 mm dry blood specimens obtained from the Danish Newborn Screening Biobank.

The population of coded specimens contained eleven T cell deficient specimens; all were correctly identified by the CD3 assay. Maternal engraftment (25%) was confirmed in one specimen that was classified as SCID and correctly identified as T cell deficient. Therefore, Applicants have significantly improved the performance of the CD3 assay.

Testing for SCID has recently become of interest to the newborn screening (NBS) community, because the detection of this condition in early infancy is crucial for effective treatment. Several newborn screening programs have implemented screening for this condition. The current method of screening for SCID is by T-cell receptor excision circles (TREC) assay (Chan K, and Puck J M. J Allergy Clin Immunol 2005; 115:391-8; Baker M W et al. J Allergy Clin Immunol 2009; 124:522-7 and Gerstel-Thompson J L et al. Clin Chem 2010; 56:1466-74), which detects the presence or absence of an excised segment of DNA. However, molecular techniques are not routinely adapted in many NBS laboratories, where an immunoassay would be preferred. Thus, as recently reported (Janik D K et al. J Clin Chem 2010:56(9): 1460-69), Applicants developed an immunoassay that provides an alternative method to TREC testing that quantifies CD3. The rational of Applicants' choice for CD3 is that it is part of the T cell receptor complex on mature T cells; therefore CD3 can be used as a marker for the presence or absence of T cells (Dave VP. Immunol Rev 2009; 232:22-33). Low or absent T cells in peripheral blood is a common characteristic of T cell immunodeficiencies and all but one form of severe combined immunodeficiency (SCID) (Edgar JDM. J Clin Pathol 2008; 61:988-93). In Applicants' previous report Applicants had a very limited number of positive SCID specimens for validation. Here, Applicants report the validation of an improved immunoassay in which Applicants use a custom designed avian anti-human CD3 antibody that shows superior performance to the previously used commercial antibody on specimens from SCID affected patients obtained from The Danish Newborn Screening Biobank (Norgaard-Pedersen B et al. J Inherit Metab Dis. 2007; 30: 530-6).

Specimens were retrieved from The Danish Newborn Screening Biobank. The study was accepted by The Danish Data protection Agency (no: 2010-41-4335), by The Steering Committee for the Newborn Screening Biobank and the New York State Department of Health's IRB 00-402. All specimens were coded and the diagnosis was not known to us until testing was completed.

The anti-human CD3 capture antibody was purchased from USbiological. The IgY anti-human CD3 detection antibody was made in chicken via Invitrogen's (Carlsbad, Calif.) custom antibody service and delivered at a stock concentration of 1 mg/mL. Other reagents used were: Sulfo-NHS-LC-biotin (Pierce, Rockford, Ill.); streptavidin-Phycoerytherin (Prozyme, Hayward, Calif.); phosphate buffered saline+Tween 20, protease inhibitor cocktail, gelatin, and Histopaque 1077 (Sigma, St. Louis, Ill.); whole and leuko-depleted blood units (Tennessee Blood Services, Memphis, Tenn.); carboxylated xMAP microspheres (Luminex Corp., Austin, Tex.); low protein binding 96-well filter bottom plates (Millipore, Billerica, Mass.), flat bottom microtiter plates (Corning, Corning, N.Y.); pooled human serum (BioResource Technology, East Greenwich, R.I.); triton-x114 (MP Bioscience, Solon, Ohio), and Ahlstrom grade 226 specimen collection paper (ID Biological Systems, Greenville, S.C.)

Anti-CD3 specific capture monoclonal antibodies were coupled to Luminex xMAP microspheres following the protocol provided by Luminex (http://www.luminexcorp.com/support/protocols/index.html). Using techniques previously described (Bellisario R et al. Clin Chem 2000; 46:1422-4; Bellisario R et al. Early Hum Dev 2001; 64:21-25 and Lindau-Shepard B A and Pass K A. Clin Chem. 2010. 56:3: 445-450), 25-100 μg of anti-CD3 capture monoclonal antibody was coupled to $5\times10^6$ Luminex microspheres, region 132 (L-100-C132-04). The anti-CD3 polyclonal antibody was biotinylated with sulfo-NHS-LC-biotin according to the manufacturer's instructions (Pierce, Rockford, Ill.).

Whole blood was used to prepare calibrators and controls, after determining leukocyte counts by flow cytometry. Leukocytes were collected from whole blood by use of Histopaque 1077, according to the manufacturer's instructions, counted on a hemacytometer, and resuspended at a concentration of $30\times10^6$ cells/mL in human serum containing 2% protease inhibitor cocktail. To make standards, two-fold serial dilutions of the $30\times10^6$ cells/mL suspension were carried out in human serum containing protease inhibitors to achieve a final leukocyte concentration of $0.234\times10^6$ cells/mL.

Leukocyte-reduced blood was examined by flow cytometry to confirm the absence of CD3 and CD45 positive cells. Packed red blood cells were made by washing leukocyte-reduced blood four times with phosphate buffered saline (PBS), pH 7.4 with centrifugation at 3000 g for 30 min. An equal volume of packed red blood cells (RBC) was added to each dilution to achieve a hematocrit of 50%. The leukocyte-enriched blood (75 μL) was spotted on Ahlstrom Grade 226 specimen collection paper and dried overnight. Dried spots were wrapped in foil and stored in a sealable bag with desiccant at −20° C. Controls were made from whole adult blood, with lymphocytes previously measured by flow cytometry.

Enhancement to the protocol from the previously published assay (Janik D K et al. J Clin Chem 2010:56(9):1460-69) included replacing the commercially available anti-CD3 detection antibody with a custom made IgY anti-CD3 detection antibody used at a concentration of 0.25 mg/L, and the incubation time of blood eluate and microspheres was reduced from 3 hours to 2 hours and the amplification step and its associated wash steps have been removed. The enhanced assay protocol consisted of six steps with washings between each step; incubation of eluate and microspheres, wash, incubation with detection antibody, wash, incubation with streptavidin phycoerythrin, wash, resuspend and read.

Figure 6:
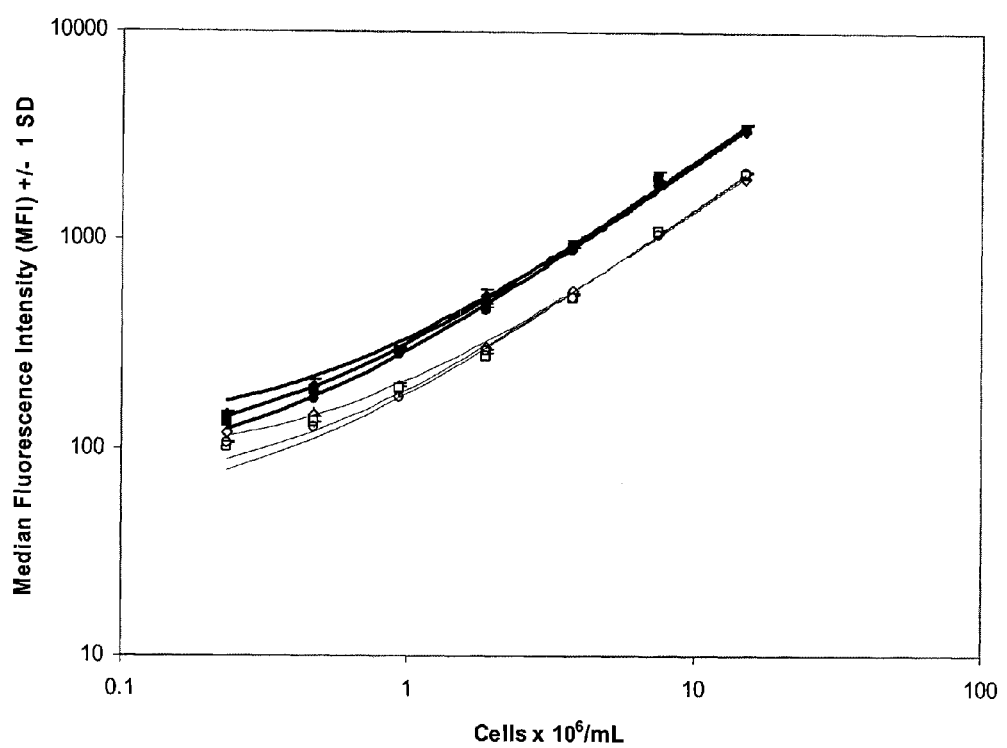
FIG. 6 depicts an IgG and IgY comparison where three plates with four replicates for each standard per plate were assayed in series, IgG is shown with open symbols and linear fit gave r2 values of 0.996 or greater for all of the calibration curves.

Standard curve comparison of the commercial CD3 detection antibody to the IgY detection antibody showed a broader linear detection range for the IgY antibody. The chicken antibody required less incubation time and required fewer reagents per sample. The IgY detection antibody had a linear range from $0.2 \times 10^6$ to $15 \times 10^6$ T cells/mL, while the commercial antibody had a linear range of $1.0 \times 10^6$ to $7.5 \times 10^6$ T cells/mL (FIG. 6).

Applicants measured the CD3 concentration of 124 coded neonate dry blood spots obtained from The Danish Newborn Screening Biobank. Mean fluorescent intensities were converted to concentrations of CD3 using the LiquiChip program.

Figure 7:
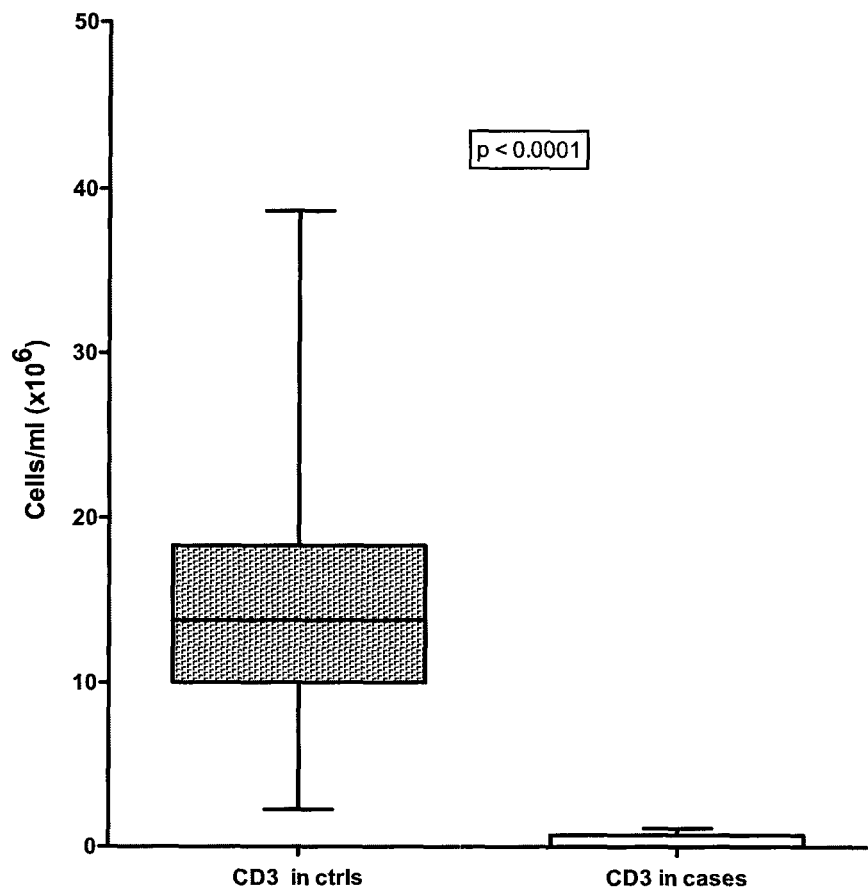
FIG. 7 depicts calculated concentrations of T cells for the control and positive specimens provided by The Danish National Newborn Screening Biobank.

The decoded results revealed that normal infant samples had T cell counts which ranged from $2.14 \times 10^6$/mL to $27.8 \times 10^6$/mL, while samples from affected infants ranged from $0.03 \times 10^6$/mL to $1.07 \times 10^6$/mL (FIG. 7). Eleven samples were from infants with T cell related immunodeficiencies (FIG. 8); eight of the eleven samples were a form of SCID, one sample was SCID with 25% maternal engraftment and the remaining two specimens were diagnosed with Omenn syndrome and Wiskott Aldrich syndrome. Four control samples were labeled as High and 5 of the affected samples were labeled as Low. A value of High or Low by the Liquichip software indicates that the measured MFI values were too high or too low to extrapolate a concentration.

In Applicants' previously described immunoassay (Janik D K et al. J Clin Chem 2010:56(9):1460-69) Applicants utilized the most effective detection antibody that was commercially available. However, because of lot to lot variation and availability issues Applicants felt a more reliable supply of antibody was necessary to make a dependable assay. Applicants contracted for the production of antigen specific avian (chicken) antibodies (IgY) to human CD3 because IgY antibodies have been shown to be stable for long term storage and do not bind to human Fc receptors, rheumatoid factor or complement, thus, nonspecific binding of interfering substances is greatly reduced. IgY antibodies are purified from chicken egg yolks with an egg laying hen producing enough eggs in a week to purify antibodies equivalent to the amount of antibodies in 75-90 mL of mammalian serum (Larsson A. et al. Poultry Science. 1993. 72(10):1807-12). Indeed, Applicants' study demonstrates that the custom IgY antibodies to CD3 have low background and are highly specific.

To date, the CD3 immunoassay Applicants developed using these antibodies has been able to correctly identify specimens with low or undetectable T cells from various SCID forms, Wiskott-Aldrich Syndrome, Ommen Syndrome and two SCID specimens with maternal engraftment. With the enhanced performance and ability of the CD3 assay to correctly identify T cell deficiency, it should be considered a complimentary or alternative to other dry blood spot T cell detection techniques.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. An isolated CD3 epsilon peptide consisting of 12 residues wherein residues 8-12 of the peptide are residues 8-12 of SEQ ID NO: 1.

2. An isolated CD3 epsilon peptide consisting of SEQ ID NO: 1.

* * * * *

SEQUENCE LISTING

```
<160> NUMBER OF SEQ ID NOS: 24

<210> SEQ ID NO 1
<211> LENGTH: 12
<212> TYPE: PRT
<213> ORGANISM: Homo sapiens

<400> SEQUENCE: 1

Ala Lys Ala Lys Pro Val Thr Arg Gly Ala Gly Ala
1               5                   10

<210> SEQ ID NO 2
<211> LENGTH: 10
<212> TYPE: PRT
<213> ORGANISM: Homo sapiens

<400> SEQUENCE: 2

Leu Tyr Ser Gly Leu Asn Gln Arg Arg Ile
1               5                   10

<210> SEQ ID NO 3
<211> LENGTH: 12
<212> TYPE: PRT
```

<213> ORGANISM: Gallus sp.

<400> SEQUENCE: 3

Val Lys Ala Lys Pro Val Thr Arg Gly Ala Gly Ala
1               5                   10

<210> SEQ ID NO 4
<211> LENGTH: 12
<212> TYPE: PRT
<213> ORGANISM: Gallus sp.

<400> SEQUENCE: 4

Ala Ala Ala Lys Pro Val Thr Arg Gly Ala Gly Ala
1               5                   10

<210> SEQ ID NO 5
<211> LENGTH: 12
<212> TYPE: PRT
<213> ORGANISM: Gallus sp.

<400> SEQUENCE: 5

Ala Lys Val Lys Pro Val Thr Arg Gly Ala Gly Ala
1               5                   10

<210> SEQ ID NO 6
<211> LENGTH: 12
<212> TYPE: PRT
<213> ORGANISM: Gallus sp.

<400> SEQUENCE: 6

Ala Lys Ala Ala Pro Val Thr Arg Gly Ala Gly Ala
1               5                   10

<210> SEQ ID NO 7
<211> LENGTH: 12
<212> TYPE: PRT
<213> ORGANISM: Gallus sp.

<400> SEQUENCE: 7

Ala Lys Ala Lys Ala Val Thr Arg Gly Ala Gly Ala
1               5                   10

<210> SEQ ID NO 8
<211> LENGTH: 12
<212> TYPE: PRT
<213> ORGANISM: Gallus sp.

<400> SEQUENCE: 8

Ala Lys Ala Lys Pro Ala Thr Arg Gly Ala Gly Ala
1               5                   10

<210> SEQ ID NO 9
<211> LENGTH: 12
<212> TYPE: PRT
<213> ORGANISM: Gallus sp.

<400> SEQUENCE: 9

Ala Lys Ala Lys Pro Val Ala Arg Gly Ala Gly Ala
1               5                   10

<210> SEQ ID NO 10
<211> LENGTH: 12
<212> TYPE: PRT
<213> ORGANISM: Gallus sp.

<400> SEQUENCE: 10

```
Ala Lys Ala Lys Pro Val Thr Ala Gly Ala Gly Ala
1               5                   10
```

<210> SEQ ID NO 11
<211> LENGTH: 12
<212> TYPE: PRT
<213> ORGANISM: Gallus sp.

<400> SEQUENCE: 11

```
Ala Lys Ala Lys Pro Val Thr Arg Ala Ala Gly Ala
1               5                   10
```

<210> SEQ ID NO 12
<211> LENGTH: 12
<212> TYPE: PRT
<213> ORGANISM: Gallus sp.

<400> SEQUENCE: 12

```
Ala Lys Ala Lys Pro Val Thr Arg Gly Val Gly Ala
1               5                   10
```

<210> SEQ ID NO 13
<211> LENGTH: 12
<212> TYPE: PRT
<213> ORGANISM: Gallus sp.

<400> SEQUENCE: 13

```
Ala Lys Ala Lys Pro Val Thr Arg Gly Ala Ala Ala
1               5                   10
```

<210> SEQ ID NO 14
<211> LENGTH: 12
<212> TYPE: PRT
<213> ORGANISM: Gallus sp.

<400> SEQUENCE: 14

```
Ala Lys Ala Pro Val Thr Glu Arg Gly Ala Gly Val
1               5                   10
```

<210> SEQ ID NO 15
<211> LENGTH: 10
<212> TYPE: PRT
<213> ORGANISM: Gallus sp.

<400> SEQUENCE: 15

```
Ala Tyr Ser Gly Leu Asn Gln Arg Arg Ile
1               5                   10
```

<210> SEQ ID NO 16
<211> LENGTH: 10
<212> TYPE: PRT
<213> ORGANISM: Gallus sp.

<400> SEQUENCE: 16

```
Leu Ala Ser Gly Leu Asn Gln Arg Arg Ile
1               5                   10
```

<210> SEQ ID NO 17
<211> LENGTH: 10
<212> TYPE: PRT
<213> ORGANISM: Gallus sp.

<400> SEQUENCE: 17

```
Leu Tyr Ala Gly Leu Asn Gln Arg Arg Ile
1               5                   10
```

<210> SEQ ID NO 18
<211> LENGTH: 10
<212> TYPE: PRT
<213> ORGANISM: Gallus sp.

<400> SEQUENCE: 18

Leu Tyr Ser Ala Leu Asn Gln Arg Arg Ile
1               5                   10

<210> SEQ ID NO 19
<211> LENGTH: 10
<212> TYPE: PRT
<213> ORGANISM: Gallus sp.

<400> SEQUENCE: 19

Leu Tyr Ser Gly Ala Asn Gln Arg Arg Ile
1               5                   10

<210> SEQ ID NO 20
<211> LENGTH: 10
<212> TYPE: PRT
<213> ORGANISM: Gallus sp.

<400> SEQUENCE: 20

Leu Tyr Ser Gly Leu Ala Gln Arg Arg Ile
1               5                   10

<210> SEQ ID NO 21
<211> LENGTH: 10
<212> TYPE: PRT
<213> ORGANISM: Gallus sp.

<400> SEQUENCE: 21

Leu Tyr Ser Gly Leu Asn Ala Arg Arg Ile
1               5                   10

<210> SEQ ID NO 22
<211> LENGTH: 10
<212> TYPE: PRT
<213> ORGANISM: Gallus sp.

<400> SEQUENCE: 22

Leu Tyr Ser Gly Leu Asn Gln Ala Arg Ile
1               5                   10

<210> SEQ ID NO 23
<211> LENGTH: 10
<212> TYPE: PRT
<213> ORGANISM: Gallus sp.

<400> SEQUENCE: 23

Leu Tyr Ser Gly Leu Asn Gln Arg Ala Ile
1               5                   10

<210> SEQ ID NO 24
<211> LENGTH: 10
<212> TYPE: PRT
<213> ORGANISM: Gallus sp.

<400> SEQUENCE: 24

Leu Tyr Ser Gly Leu Asn Gln Arg Arg Ala
1               5                   10